United States Patent
Johdo et al.

(10) Patent No.: US 6,653,455 B1
(45) Date of Patent: Nov. 25, 2003

(54) CRYSTALLIZATION OF DOXORUBICIN HYDROCHLORIDE

(75) Inventors: Osamu Johdo, Fujisawa (JP); Takuma Nakao, Yokohama (JP); Takeo Yoshioka, Ayase (JP)

(73) Assignee: Mercian Corporation, Tokyo (JP)

( * ) Notice: Subject to any disclaimer, the term of this patent is extended or adjusted under 35 U.S.C. 154(b) by 0 days.

(21) Appl. No.: 09/807,451

(22) PCT Filed: Oct. 15, 1999

(86) PCT No.: PCT/JP99/05699

§ 371 (c)(1),
(2), (4) Date: Apr. 13, 2001

(87) PCT Pub. No.: WO00/23453

PCT Pub. Date: Apr. 27, 2000

(30) Foreign Application Priority Data

Oct. 16, 1998 (JP) .......................................... 10-309542

(51) Int. Cl.$^7$ .............................................. C07H 15/24
(52) U.S. Cl. .......................................... 536/6.4; 514/34
(58) Field of Search ................. 536/6.4, 16.9; 514/34

(56) References Cited

U.S. PATENT DOCUMENTS 4,861,870 A   8/1989   Oppico et al. ............. 536/16.9

FOREIGN PATENT DOCUMENTS

| GB | 1161278 | 8/1969 |
| GB | 1457632 | 12/1976 |
| HU | 204 570 B | * 4/1991 |
| HU | 204 570 | 1/1992 |

OTHER PUBLICATIONS

Database CA "Online!", Chemical Abstracts Service, Columbus, Ohio, U.S.A., Database Accession No. 115:47771 XP002179140.

* cited by examiner

*Primary Examiner*—James O. Wilson
*Assistant Examiner*—Howard V. Owens. Jr.
(74) *Attorney, Agent, or Firm*—Wenderoth, Lind & Ponack, Ltd.

(57) ABSTRACT

Disclosed are a crystallizing method of doxorubicin hydrochloride from a doxorubicin hydrochloride-containing solution, particularly a method for carrying out the crystallization under a condition of 40° C. or higher, and a doxorubicin hydrochloride crystalline aggregate having particularly an excellent solubility in water.

2 Claims, No Drawings

CRYSTALLIZATION OF DOXORUBICIN HYDROCHLORIDE

TECHNICAL FIELD

The present invention relates to a crystallizing method of doxorubicin hydrochloride and a crystalline aggregate of doxorubicin hydrochloride having a fixed characteristic.

BACKGROUND

Doxorubicin (or called adriamycin) is an antibiotic represented by the following formula:

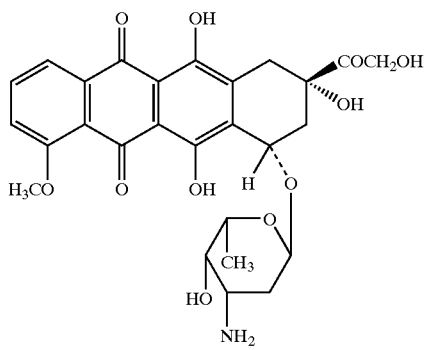

and produced from *streptomyces peuceticus var caestius*. Also, doxorubicin is provided as well by chemical conversion of daunorbicin (or called daunomycin). This hydrochloride (that is, doxorubicin hydrochloride) has a broad anticancer spectrum and has an excellent efficacy in chemical therapy of malignant lymphoma, pulmonary cancer, digestive cancer and mammary cancer. As a matter of fact, a liquid preparation of doxorubicin hydrochloride (a preparation for injection and a solution of saline) is widely used for clinical therapy of the various cancers described above.

Powdery or crystalline doxorubicin hydrochloride is provided as a raw material for such liquid preparations, but those which can be available at present are not necessarily satisfactory in terms of solubility in water. In particular, when a liquid preparation is prepared at a therapy site immediately before use, solid doxorubicin hydrochloride which is more quickly dissolved in water shall be desired to be provided.

On the other hand, powdery or crystalline doxorubicin hydrochloride is obtained usually by precipitation or crystallization from an organic solvent system or a water-based solvent system containing an organic solvent, but it is difficult to reduce or remove the residual solvent or the intended crystals have a low yield in many cases.

Solid doxorubicin hydrochloride which is commercially available for medical use at present contains less amount of residual solvents than allowed for a use purpose thereof, but some of them requires about 10 minutes until they are dissolved by stirring treatment in water at, an ambient temperature (25° C.). In addition thereto, the small undissolved remainder is observed in a certain case even after a large part thereof is dissolved in water. A standard product of USP (available from Japan Koteisho Association; 2-12-5, Shibuya, Shibuya-ku, Tokyo) is especially excellent in a solubility in water. In this case, however, the small undissolved remainder is observed so often after dissolving treatment.

DISCLOSURE OF THE INVENTION

Accordingly, an object of the present invention is to provide a crystallizing method which is excellent in reducing a residual solvent as well as raising the yield in crystallization and can produce a finished doxorubicin hydrochloride product having a high solubility in water, and a doxorubicin hydrochloride crystalline aggregate having such characteristic as described above.

A crystallizing method of doxorubicin hydrochloride has been investigated by the present inventors, and it has been found by them that the object described above can be achieved by carrying out crystallization in a specific solvent system at some fixed temperature or higher, which is different from a usual common sense (refer to, for example, Japanese Patent Application Laid-Open No. 118797/1984 or U.S. Pat. No. 4,861,870).

Accordingly, the present invention relates to a crystallizing method of doxorubicin hydrochloride from a doxorubicin hydrochloride-containing solution, wherein the doxorubicin hydrochloride-containing solution is a water-based solution containing doxorubicin and a poor solvent to doxorubicin, and the crystallization is carried out at a temperature of 40° C. or higher.

Further, the present invention relates to a crystalline aggregate of doxorubicin hydrochloride having characteristics that:

(A) moisture content accounts for 2% by weight or less and the other total residual solvents account for 1.5% or less, (B) the average particle diameter is 15 μm or more in terms of a circle-corresponding diameter determined by image projection, and (C) the aggregate has such a solubility that it is substantially completely dissolved in water in about 2 minutes or shorter under a stirring condition at 25° C.

BEST MODE FOR CARRYING OUT THE INVENTION

Doxorubicin hydrochloride (hereinafter referred to as DOX.HCl) which can be used for the crystallizing method according to the present invention may be any one regardless of a production process and a refining step thereof as long as it has a fixed or higher purity. That is, the crystallizing method of the present invention can be used in a preliminary refining step for obtaining roughly refined DOX.HCl and a final refining step for obtaining a finished product. However, the crystallizing method according to the present invention is used suitably in a final refining step of DOX.HCl considering actions and effects such as easiness of a reduction in the residual solvent and obtainability of the crystals having a high solubility in water. Accordingly, the present invention shall be explained below taking primarily use in the final refining step into consideration, but it should be understood that the present invention shall not be restricted thereto.

A DOX.HCl-containing solution used for the crystallizing method according to the present invention is a water-based solution containing doxorubicin (hereinafter referred to as DOX) and a poor solvent to DOX.HCl. In preparing such water-based solution, DOX.HCl is first dissolved in water or DOX is dissolved in a diluted hydrochloric acid aqueous solution (for example, 0.001N HCl), and in some cases, water-miscible organic solvents including a poor solvent which shall be described later may be contained in the aqueous solution described above. Next, the DOX.HCl-containing aqueous solution (hereinafter referred to as a dissolved solution) thus prepared is usually mixed with a poor solvent to DOX.HCl. This mixing may be carried out either by mixing the DOX.HCl-containing aqueous solution with the poor solvent in one lot or adding the former little by little to the latter or in contrast with this, adding the latter little by little to the former.

The poor solvent may be any ones as long as they meet the, object of the present invention, and capable of being usually given are methanol, ethanol isopropanol, acetonitrile, acetone and mixed solvents of two or more kinds thereof. Among them, ethanol, acetone and a mixed solvent of ethanol and acetone are preferred, and out of them, ethanol and a mixed solvent of ethanol and acetone are particularly preferred. Preferred is the mixed solvent of ethanol and acetone in which they are mixed in a proportion ethanol to acetone of 4:1 to 1:1, particularly 2.5:1.

On the other hand, the organic solvent contained in the dissolved solution described above may be any of the poor solvents described above. However, water (acid water) mixed with ethanol is preferred, and in this case, water mixed with ethanol in a proportion water to ethanol of 7.5:5 to 7.5:15 is particularly preferred.

Among such solvent systems, particularly preferred is a combination of the solvent systems in which the solvent contained in the dissolved solution described above comprises water and ethanol in the preferred proportion and the poor solvent comprises ethanol and acetone in the preferred proportion.

Such combination of the dissolved solution and the poor solvent can be varied according to the content of DOX.HCl. In general, the dissolved solution to the poor solvent stays in a proportion of 1:2 to 1:10, preferably about 1:5.

The DOX.HCl-containing solution comprising such solvent system may stay in a state in which DOX.HCl is dissolved before the crystallization, and a concentration of DOX.HCl shall not be restricted. In general, however, a concentration of 8 to 4.5 (weight/volume) % up to 10 (weight/volume) % of DOX.HCl is preferred.

According to the present invention, a temperature for carrying out the crystallization has to be set to 40° C. or higher. When the DOX.HCl-containing solution is prepared at 40° C. or higher, this temperature may be maintained as it is or reduced a little. Usually, the DOX.HCl-containing solution is prepared at 5 to 35° C., and the temperature is elevated from this temperature to 40° C. or higher to carry out the crystallization. The temperature is 40° C. or higher, preferably 45 to 75° C. and particularly preferably 50 to 65° C. According to the present invention, the DOX.HCl-containing solution may be placed at a temperature falling in the temperature range described above in any perilod during the crystallization, and the DOX.HCl-containing solution is preferably stirred or left for standing in the temperature range described above through the whole crystallization step. The crystallization temperature may be varied in the temperature range described above but is preferably set to almost a fixed temperature for convenience of operation.

Time required for the crystallization can be selected from time required for obtaining crystals of intended DOX.HCl at a desired yield according to the solvent system used. Under the preferred conditions described above, however, intended DOX.HCl is obtained at a high yield usually in one hour or longer, preferably 2 to 24 hours and 2.5 to 5 hours in a certain case.

Thus, the crystals of intended DOX.HCl are formed. These crystals are separated from the crystallization solution, gathered and dried.

The crystals described above which are obtained by the crystallizing method of the present invention have an average particle diameter of about 15 μm or more and are very narrow in a particle distribution, and therefore they can conveniently be separated and gathered by filtration using a suitable filter. However, it shall not be restricted thereto, and other conventionally known separating means can be used as well.

Any means can be selected as the drying means as long as it does not an adverse effect on a biological activity of DOX.HCl. In general, drying is carried out preferably by a vacuum (reduced pressure) drying method. Air-drying may be carried out at an ambient temperature prior to vacuum drying. The temperature in carrying out vacuum drying can be set to 5 to 75° C., preferably 40 to 60° C., and a degree of a reduction in the pressure can optionally be selected. When those having a titer of about 97% or more (reduced to dried materials) determined by an HPLC method are used as the raw materials used for the crystallization, the vacuum-drying time is set to one hour or longer, whereby usually obtained are the products which pass a purity test (according to HPLC), a residual solvent test (according to GC) and a titer test (according to HPLC) each required as USP (DOX.HCl of USP 23) standards.

The DOX.HCl crystals obtained through the crystallizing method according to the present invention can provide a crystalline aggregate having the following characteristics as the whole crystal even when dried by vacuum drying, for example, under a reduced pressure of 5 to 10 mm Hg at 40° C. for 4 hours:

(A) moisture content accounts for 2% by weight or less, and the other total residual solvents account for 1.5% or less, (B) the average particle diameter is 15 μm or more in terms of a circle-corresponding diameter determined by image projection, and (C) the aggregate has such a solubility that it is substantially completely dissolved in water in about 2 minutes or shorter under a stirring condition of 25° C. The "crystalline aggregate" described in the present invention means merely a mass of each crystal, in which the respective crystals are not coagulated by virtue of a specific physical bonding power.

Such crystalline aggregate is a novel crystalline aggregate which can clearly be distinguished from known DOX.HCl in terms of a significantly high solubility as compared with those of commercially available products including DOX-.HCl crystalline aggregates which can be available from preceding Japan Koteisho Association as USP standard products.

Accordingly, the crystalline aggregate described above also is one embodiment of the present invention. When ethanol and acetone are used as the poor solvents in the crystallizing method of the present invention, capable of being provided is the crystalline aggregate described above having a moisture content of about 1% or less, an acetone content of about 0.4% or less and an ethanol content of about 1.0% or less based on the whole weight of the crystalline aggregate. Such crystalline aggregate is the preferred embodiment of the present invention.

The crystalline aggregate according to the present invention includes a further preferred embodiment in which the solubility described above is 1.5 to 2 minutes or shorter than it.

In addition thereto, the DOX.HCl crystalline aggregate according to the present invention is characterized by that while it has a hygroscopicity which is equivalent to or lower than those of the USP standard products, it shows such a good solubility as described above.

Thus, according to the present invention, disclosed are a novel crystallizing method capable of providing the DOX.HCl crystalline aggregate which is suitable for providing a liquid preparation of DOX.HCl, and a crystalline aggregate.

The present invention shall more specifically be explained below with reference to specific examples, but these examples have a purpose only to facilitate understanding of the present invention and do not intend to limit the present invention to these examples.

Methods for Determining Various Characteristics Described in the Present Invention <Solubility Test>

A beaker of 20 ml (minor diameter: 30 mm) was charged with 5 ml of water and then 50 mg of a DOX.HCl crystal sample, and the sample was stirred at 25° C. and about 600 rounds/minute by means of a magnetic stirrer (diameter 6 mm×length 10 mm). Time consumed until the sample was completely dissolved was measured wile observing the dissolving state every 30 seconds with naked eyes.

<Measurement of Residual Solvent> a) A moisture in 10 to 15 ml of the sample was determined by means of an AQ-6 type trace amount moisture-measuring apparatus manufactured by Hiranuma Sangyo Co., Ltd. according to a coulometric titration method. In determining, used respectively were HYDRANAL-Coulomat AK/for acetone (Kobayashi Pure Chemical Ind. Co., Ltd.) for a generating solution and HYDRANAL-Coulomat CG-K/for acetone (Kobayashi Pure Chemical Ind. Co., Ltd.) for a counter electrode solution.

b) A poor solvent amount was determined by the following gas chromatography (a head space method). DB-WAX manufactured by J & W Co., Ltd. was installed as a column in a gas chromatograph GC-14A (equipped with a flame ionization detector (FID)) (manufactured by Shimadzu Mfg. Co., Ltd.), and the sample was analyzed by a head space method on a condition that helium having a flow amount of about 1.0 ml/minute was used to calculate a poor solvent amount contained in the sample.

<Hygroscopicity>

Determined by the following cup method. To be specific, about 15 to 20 mg of the sample was put in a cylindrical cup having a diameter of 6 mm and a depth of 6 mm and left standing at a fixed temperature (25° C.) and relative humidity (50 to 60% RH) for 15 minutes to measure a weight change, whereby the hygroscopicity was evaluated.

In the following respective examples, a weight-increasing rate of 0.40% or more is shown by an evaluation criterion that the hygroscopicity is large (−); a weight-increasing rate of 0.20% or more and less than 0.40% is shown by an evaluation criterion that the hygroscopicity is ;intermediate (±); and a weight-increasing rate of less than 0.20% is shown by an evaluation criterion that the hygroscopicity is small: (+).

<Average Particle Diameter>

The average particle diameter is shown by a diameter of a circle having the same area as an injected area of the particle, a so-called Heywood diameter (circle-corresponding diameter) according to a microscopic method (injected image).

Method

A small amount of the crystals was put on a slide glass, and 1 to 2 drops of a hydrophilic surfactant (sesquioleic acid sorbitan) were fallen thereon to disperse them. It was photographed by means of a polarization microscope (photographing lens: 3.3 magnifications, objective lens: 20 magnifications) equipped with a photographing device. Optional 10 pieces of the typical crystals were selected on the photograph to measure a long diameter and a short diameter thereof An (projected) area of the particle was shown by long diameter×short diameter, and the particle diameter was shown by a diameter of a circle having the same area as that obtained above.

Examples 1 to 59

Crystallization and Sampling of Crystals

A prescribed amount of DOX.HCl (titer: about 960 to 980 µg/mg) was dissolved at a room temperature (about 25° C.) in dissolved solution systems described in the following Table I to which 0.001N hydrochloric acid was added if necessary, and then the solutions were filtered through absorbent cotton. The filtrates were put together with poor solvents and heated to a prescribed temperature, and then they were stirred (200 rpm) for about one hour. Precipitated crystals were filtered and washed with 10 ml of the poor solvent, and they were dried at 40° C. under vacuum (5 to 10 mm Hg) through a night.

Summarized in Tables I to II respectively are the amounts of DOX.HCl used in the respective examples, the solvent amounts, the mixing ratios (volume/volume) in the case of the mixed solvents, the adding methods of the solvents (solution→poor: the dissolved solution was added to the poor solvent; poor→solution: the poor solvent was added to the dissolved solution; and poor→solution/numerical value min and solution→poor/numerical value min mean the poor solvents and the dissolved solutions were added little by little in time (minute) of the numerical values), the crystallization temperatures (° C.), the stirring speeds (rpm) in the crystallization, the yields (%), the moisture (%), the contents of the respective poor solvents and the average article diameters (µm). In the tables, A means acetone; E means ethanol; AN means acetonitrile; and IP means isopropanol. The term 25→60 in the crystallization temperature means that the temperature was elevated from 25° C. to 60° C. (about 3.5° C./minute). Null columns in the tables mean that measurement was not carried out. In Table II, the moistures (%) represent moisture contents, and A (%) and E (%) represent the contents of the poor solvents. When the contents of the poor solvents are shown for acetonitrile and isopropanol, they are described otherwise.

TABLE I

| | | | Crystallization conditions | | |
|---|---|---|---|---|---|
| Example | DOX.HCl (mg) | Resolvents | Poor solvent | Adding method | Crystallization temperature |
| 1 | 499.4 | Water (12.5 ml) | A (250 ml) | Solution → poor | 0 |
| 2 | 497.4 | Acid water (12.5 ml) | A (250 ml) | Solution → poor | 0 |

TABLE I-continued

Crystallization conditions

| Example | DOX.HCl (mg) | Resolvents | Poor solvent | Adding method | Crystallization temperature |
|---|---|---|---|---|---|
| 3 | 505.2 | Acid water (12.5 ml) | A (250 ml) | Poor → solution | 0 |
| 4 | 508.6 | Acid water (12.5 ml) | A (250 ml) | Poor → solution | 25 |
| 5 | 500 | Acid water (12.5 ml) | A/E (2:1) (125 ml) | Poor → solution | 5 |
| 6 | 500 | Acid water (12.5 ml) | A/E (3:1) (125 ml) | Poor → solution | 5 |
| 7 | 500 | Acid water (12.5 ml) | A/E (4:1) (125 ml) | Poor → solution | 5 |
| 8 | 1003 | Acid water (12.5 ml) | A/E (4:1) (125 ml) | Poor → solution | 5 |
| 9 | 1000.1 | Acid water/E (1:1) (25 ml) | A/E (4:1) (112.5 ml) | Poor → solution | 5 |
| 10 | 498.6 | Acid water (12.5 ml) | A/E (2:1) (125 ml) | Poor → solution | 25 |
| 11 | 501.6 | Acid water (12.5 ml) | A/E (3:1) (125 ml) | Poor → solution | 25 |
| 12 | 504.8 | Acid water (12.5 ml) | A/E (4:1) (125 ml) | Poor → solution | 25 |
| 13 | 1003 | Acid water/E (1:1) (25 ml) | A/E (1:2) (112.5 ml) | Poor → solution | 25 |
| 14 | 1002.3 | Acid water/E (1:1) (25 ml) | A/E (1:1) (112.5 ml) | Poor → solution | 25 |
| 15 | 1003.4 | Acid water/E (1:1) (25 ml) | A/E (3:2) (112.5 ml) | Poor → solution | 25 |
| 16 | 1001.1 | Acid water (12.5 ml) | A/E (2:1) (125 ml) | Poor → solution | 25 |
| 17 | 1000.7 | Acid water (12.5 ml) | A/E (3:1) (125 ml) | Poor → solution | 25 |
| 18 | 1001.3 | Acid water (12.5 ml) | A/E (4:1) (125 ml) | Poor → solution | 25 |
| 19 | 1002.8 | Acid water/E (1:1) (25 ml) | A/E (1:2) (112.5 ml) | Poor → solution | 40 |
| 20 | 1002.9 | Acid water/E (1:1) (25 ml) | A/E (2:1) (112.5 ml) | Poor → solution | 40 |
| 21 | 1003.5 | Acid water/E (1:1) (25 ml) | A/E (2:2.3) (112.5 ml) | Poor → solution | 60 |
| 22 | 1001.5 | Acid water/E (1:1) (25 ml) | A/E (1:1.2) (112.5 ml) | Poor → solution | 60 |
| 23 | 1005.1 | Acid water/E (1:1) (25 ml) | E (112.5 ml) | Solution → poor | 60 |
| 24 | 1001.2 | Acid water/E (1:1) (25 ml) | E (112.5 ml) | Poor → solution | 60 |
| 25 | 1001.5 | Acid water/E (1:1) (25 ml) | A/E (1:1.2) (112.5 ml) | Poor → solution/100 rpm | 60 |
| 26 | 1006.4 | Acid water/E (1:1) (25 ml) | A/E (1:1.2) (112.5 ml) | Poor → solution/200 rpm | 60 |
| 27 | 1003.9 | Acid water/E (1:1) (25 ml) | A/E (1:1.2) (112.5 ml) | Poor → solution/300 rpm | 60 |
| 28 | 1002.2 | Acid water/E (1:1) (25 ml) | A/E (1:3) (112.5 ml) | Solution → poor | 60 |
| 29 | 1000.7 | Acid water/E (1:1) (25 ml) | A/E (1:2) (112.5 ml) | Solution → poor | 60 |
| 30 | 1003.6 | Acid water/E (1:1) (25 ml) | A/E (1:1) (112.5 ml) | Solution → poor | 60 |
| 31 | 1001.4 | Acid water/E (1:1) (25 ml) | A/E (2:1) (112.5 ml) | Solution → poor | 60 |
| 32 | 1003 | Acid water/E (1:1) (25 ml) | A/E (3:1) (112.5 ml) | Solution → poor | 60 |
| 33 | 1001.1 | Acid water/E (1:1) (25 ml) | A/E (1:2) (112.5 ml) | Poor → solution/200 rpm | 25 → 60 |
| 34 | 1000.9 | Acid water/E (1:1) (25 ml) | A/E (1:1) (112.5 ml) | Poor → solution/200 rpm | 25 → 60 |
| 35 | 1000.4 | Acid water/E (1:1) (25 ml) | A/E (2:1) (112.5 ml) | Poor → solution/200 rpm | 25 → 60 |
| 36 | 1001.3 | Acid water/E (1:1) (25 ml) | A/E (1:1) (112.5 ml) | Poor → solution/100 rpm | 25 → 60 |
| 37 | 1000.7 | Acid water/E (1:1) (25 ml) | A/E (1:2) (112.5 ml) | Solution → poor/200 rpm | 60 |
| 38 | 1001.9 | Acid water/E (2:3) (25 ml) | A/E (1:2.36) (125 ml) | Solution → poor/200 rpm | 60 |
| 39 | 1001.5 | Acid water/E (3:7) (25 ml) | A/E (1:2.42) (125 ml) | Solution → poor/200 rpm | 60 |
| 40 | 1001.4 | Acid water/E (3:7) (25 ml) | A/E (1:3.58) (125 ml) | Solution → poor/200 rpm | 60 |
| 41 | 1001.5 | Acid water/E (3:7) (25 ml) | A/E (1:2.42) (125 ml) | Solution → poor/200 rpm | 60 |
| 42 | 1000.3 | Acid water/E (3:7) (25 ml) | A/E (1:1.28) (125 ml) | Solution → poor | 60 |
| 43 | 2000 (g) | Acid water/E (2:3) (50 l) | A/E (1:3) (250 l) | Solution → poor | 65 |
| 44 | 1000.1 | Acid water/E (3:7) (25 ml) | A/E (1:3.56) (125 ml) | Solution → poor/5 min | 60 |
| 45 | 1002.6 | Acid water/E (3:7) (25 ml) | A/E (1:3.56) (125 ml) | Solution → poor/30 min | 60 |
| 46 | 1005.4 | Acid water/E (3:7) (25 ml) | A/E (1:3.56) (125 ml) | Solution → poor/60 min | 60 |
| 47 | 1002.7 | Acid water/E (3:7) (25 ml) | A/E (1:3.56) (125 ml) | Solution → poor/60 min | 40 |
| 48 | 999.7 | Acid water/E (3:7) (25 ml) | A/E (1:3.56) (125 ml) | Solution → poor/60 min | 45 |
| 49 | 1004.6 | Acid water/E (3:7) (25 ml) | A/E (1:3.56) (125 ml) | Solution → poor/60 min | 50 |
| 50 | 1000.2 | Acid water/E (3:7) (25 ml) | A/E (1:3.56) (125 ml) | Solution → poor/60 min | 55 |
| 51 | 1000.2 | Acid water/E (3:7) (25 ml) | A/E (1:3.56) (125 ml) | Solution → poor/60 hrs | 60 |
| 52 | 995.7 | Acid water/E (3:7) (25 ml) | A/E (1:3.56) (125 ml) | Solution → poor/60 min | 70 |
| 53 | 997.3 | Acid water/E (3:7) (25 ml) | A/E (1:3.56) (125 ml) | Solution → poor/3 hr | 60 |
| 54 | 1001.4 | Acid water/E (3:7) (25 ml) | A/E (1:3.56) (125 ml) | Solution → poor/1 + 2 hr | 60 → 25 |
| 55 | 999.3 | Acid water/E (2:3) (25 ml) | A/E (1:3) (125 ml) | Solution → poor | 60 |
| 56 | 1000.6 | Acid water/AN (2:3) (25 ml) | A/AN (1:3) (125 ml) | Solution → poor | 60 |
| 57 | 1000.1 | Acid water/IP (2:3) (25 ml) | A/IP (1:3) (125 ml) | Solution → poor | 60 |
| 58 | 999.8 | Acid water/AN (2:3) (25 ml) | A/AN (1:3) (125 ml) | Solution → poor | 25 |
| 59 | 999.8 | Acid water/IP (2:3) (25 ml) | A/IP (1:3) (125 ml) | Solution → poor | 25 |

TABLE II

Results after crystallization and drying

| Example | Yield (%) | Moisture (%) | A (%) | E (%) | Hygroscopicity | Average particle diameter (μm) |
|---|---|---|---|---|---|---|
| 1 | 81.6 | 0.77 | 0.54 | – | | |
| 2 | 78.4 | 1.05 | 0.58 | – | | <4 |
| 3 | 72.5 | 0.82 | 0.92 | – | | |
| 4 | 86 | 0.53 | 1.09 | – | | <4 |
| 5 | impossible to recover | | | | | |
| 6 | impossible to recover | | | | | |

TABLE II-continued

Results after crystallization and drying

| Example | Yield (%) | Moisture (%) | A (%) | E (%) | Hygro-sco-picity | Average particle diameter (μm) |
|---|---|---|---|---|---|---|
| 7 | impossible to recover | | | | | |
| 8 | 62.7 | 0.67 | 0.55 | 0.34 | − | |
| 9 | 78.1 | 0.79 | 0.53 | 0.19 | − | |
| 10 | impossible to recover | | | | | |
| 11 | impossible to recover | | | | | |
| 12 | impossible to recover | | | | | |
| 13 | 62.3 | 1 | 0.36 | 0.55 | ± | <4 |
| 14 | 74.7 | 0.55 | 0.48 | 0.43 | ± | |
| 15 | 70.2 | 0.57 | 0.55 | 0.41 | − | |
| 16 | 70.9 | 0.7 | 0.69 | 0.36 | ± | <4 |
| 17 | 63.1 | 0.62 | 0.78 | 0.3 | − | |
| 18 | 63.6 | 0.55 | 0.86 | 0.26 | − | |
| 19 | 63.6 | 0.59 | 0.35 | 0.59 | ± | 17 |
| 20 | 73 | 0.73 | 0.69 | 0.4 | + | 7 |
| 21 | 69.2 | 0.26 | 0.22 | 0.5 | + | 54 |
| 22 | 67.6 | 0.32 | 0.34 | 0.46 | + | 47 |
| 23 | 56.3 | 0.21 | | 0.78 | ± | 39 |
| 24 | 55.1 | 0.1 | | 0.71 | + | 51 |
| 25 | 67.6 | 0.32 | 0.34 | 0.46 | + | |
| 26 | 71.5 | 0.31 | 0.37 | 0.41 | + | |
| 27 | 65.7 | 0.01 | 0.37 | 0.4 | ± | |
| 28 | 57.2 | 0.4 | 0.26 | 0.64 | + | 37 |
| 29 | 69.5 | 0.06 | 0.37 | 0.65 | + | |
| 30 | 81.7 | 0.26 | 0.55 | 0.57 | + | 39 |
| 31 | 78.5 | 0.12 | 0.72 | 0.43 | + | |
| 32 | 78.8 | 0.32 | 0.71 | 0.3 | + | 34 |
| 33 | 65.3 | 0.13 | 0.33 | 0.59 | ± | 25 |
| 34 | 68.8 | 0.27 | 0.47 | 0.49 | ± | 23 |
| 35 | 93.6 | 0.23 | 0.82 | 0.48 | ± | 20 |
| 36 | 64.6 | 0.11 | 0.46 | 0.47 | ± | |
| 37 | 69.5 | 0.06 | 0.37 | 0.65 | + | |
| 38 | 71 | 0.36 | 0.35 | 0.66 | + | 28 |
| 39 | 79.6 | 0.36 | 0.4 | 0.76 | + | |
| 40 | 74.1 | 0.18 | 0.27 | 0.67 | ± | 18 |
| 41 | 79.6 | 0.36 | 0.4 | 0.76 | + | |
| 42 | 80.8 | 0.3 | 0.57 | 0.66 | + | 34 |
| 43 | 70.3 | 0.09 | 0.16 | 0.37 | + | |
| 44 | 84.4 | 0.38 | 0.29 | 0.69 | + | 28 |
| 45 | 84.3 | 0.64 | 0.26 | 0.66 | + | 46 |
| 46 | 78.1 | 0.21 | 0.12 | 0.67 | + | 86 |
| 47 | 86.8 | 0.19 | 0.43 | 0.96 | ± | 60 |
| 48 | 81.3 | 0.1 | 0.3 | 0.84 | + | 89 |
| 49 | 84.5 | 0.44 | 0.29 | 0.81 | + | 71 |
| 50 | 77.5 | 0.79 | 0.32 | 0.73 | + | |
| 51 | 76 | 0.08 | 0.25 | 0.61 | + | 73 |
| 52 | 81.1 | 0.09 | 0.19 | 0.49 | + | |
| 53 | 84.1 | 0 | 0.25 | 0.59 | + | |
| 54 | 83.4 | 1.01 | 0.2 | 0.5 | + | |
| 55 | 75.7 | 1.06 | 0.27 | 0.73 | + | 24 |
| 56 | 86.4 | 0.98 | 0.21 | 0.68* | + | 37 |
| 57 | 82.3 | 0.15 | 0.39 | 0.72** | ± | 35 |
| 58 | 88.8 | 0.72 | 0.21 | 0.58* | − | <4 |
| 59 | 88.1 | 0.05 | 0.51 | 1.00** | − | <4 |

* AN: acetonitrile
* IP: isopropanol

Among the examples described above, Examples 1 to 18, 58 and 59 are comparative examples, and Examples 19 to 57 are the examples of the present invention.

<Solubility Test>

The solubility test described above was carried out for a DXR.USP standard product (Lot J) (average particle diameter: 28 μm) as comparison and Examples 2, 46, 51, 55, 56, 57 and 58, and the results thereof are shown in Table III.

TABLE III

| Solubility in water | |
|---|---|
| Sample | Dissolving time (minute) |
| DXR.USP (comparison) | 3–3.5* |
| Example 2 | 4–4.5 |
| Example 46 | 1.5–2 |
| Example 51 | 1.5–2 |
| Example 55 | 1.5–2 |
| Example 56 | 1.5–2 |
| Example 57 | 1.5–2 |
| Example 58 | 14.5–15 |

*A large part thereof is dissolved, but a trace amount of undissolved remainder is observed.

Industrial Applicability

According to the crystallizing method of the present invention, obtained at a high yield are the doxorubicin hydrochloride crystals having more excellent characteristics as a material for producing a liquid preparation than those of a standard product of USP. In particular, these crystals are characterized by having a significantly high solubility in water. Accordingly, the present invention can be applied in the medicine-manufacturing field.

What is claimed is:

1. A method for crystallizing doxorubicin hydrochloride from a doxorubicin hydrochloride-containing solution, wherein the doxorubicin hydrochloride-containing solution is a water-based solution containing a solvent which is at least one member selected from the group consisting of methanol, ethanol, isopropanol, acetonitrile and acetone or a mixture of two or more kinds thereof and the crystallization is carried out at a temperature of 40° C. or higher, wherein a crystalline aggregate of doxorubicin hydrochloride subjected to drying treatment after the crystallization has:

(A) a moisture content of 2% by weight or less and the other total residual solvents of 1.5% or less, (B) an average particle diameter of 15 μm or more in terms of a circle-corresponding diameter determined by image projection, and (C) such a solubility that the aggregate is substantially completely dissolved in water in about 2 minutes or shorter under a stirring condition at 25° C.

2. A crystalline aggregate of doxorubicin hydrochloride having the following properties:

(A) moisture content accounts for 2% by weight or less and the other total residual solvents account for 1.5% or less, (B) an average particle diameter of 15 μm or more in terms of a circle-corresponding diameter determined by image projection, and (C) the aggregate has such a solubility that it is substantially completely dissolved in water in about 2 minutes or shorter under a stirring condition at 25° C.

* * * * *